US00PP26840P3

(12) United States Plant Patent
Ruter

(10) Patent No.: US PP26,840 P3
(45) Date of Patent: Jun. 21, 2016

(54) ***THUJA* PLANT NAMED 'RUTTHU#1'**

(50) Latin Name: *Thuja occidentalis*
Varietal Denomination: RutThu#1

(71) Applicant: University of Georgia Research Foundation, Inc., Athens, GA (US)

(72) Inventor: John M. Ruter, Bishop, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 65 days.

(21) Appl. No.: 14/121,982

(22) Filed: Nov. 10, 2014

(65) Prior Publication Data

US 2016/0135345 P1 May 12, 2016

(51) Int. Cl.
*A01H 5/00* (2006.01)

(52) U.S. Cl.
USPC ..... Plt./213

(58) Field of Classification Search
USPC ..... Plt./213
See application file for complete search history.

*Primary Examiner* — Annette Para
(74) *Attorney, Agent, or Firm* — Klarquist Sparkman, LLP

(57) ABSTRACT

A new *Thuja* plant named 'RutThu#1' is very compact with dark green foliage.

1 Drawing Sheet

STATEMENT REGARDING FEDERALLY-SPONSORED RESEARCH

This invention was made, in part, with U.S. Government support on behalf of U.S. Department of Agriculture, Hatch Act Grant. The U.S. Government has certain rights in this invention.

Latin name of the genus and species of the plant claimed: 'RutThu#1' is a rich green compact evergreen cultivar of the genus and species *Thuja occidentalis.*

Variety denomination: The new *Thuja occidentalis* claimed is of the cultivar denominated 'RutThu#1'.

BACKGROUND OF THE INVENTION

The present invention relates to a new and distinct cultivar of *Thuja occidentalis*, hereinafter referred to as 'RutThu#1'.

Pedigree and history. Seed of *Thuja occidentalis* 'Holmstrup' (unpatented) was received in 2003, cold stratified and sown. This seed was germinated at the University of Georgia Tifton Campus before being transferred in 2004 to the Center for Applied Nursery Research (CANR) in Dearing, Ga. There were thirty-five seedlings grown from this seed that were transferred to the CANR in Dearing, Ga. Five of these thirty-five plants were selected in 2005 for further evaluation. These five selected plants were planted in a field trial area in Dearing, Ga. on Feb. 27, 2006. The height and width of 'RutThu#1' at planting was 13"×12". After seven years, 'RutThu#1' was the darkest green and most compact of these five plants. Height and width measurements of 'RutThu#1' on Sep. 28, 2010 were 26"×21" and on Nov. 20, 2013 were 31"×24". In contrast, the final height and width of 'Holmstrup' variety plants of the same age growing under comparable growing conditions was 57"×48". My new plant has been asexually propagated at Dearing, Ga. by hardwood cuttings. The resulting progeny have been observed and these observations have confirmed that the distinguishing characteristics of 'RutThu#1' set forth herein are fixed in succeeding generations.

SUMMARY OF THE INVENTION

The following traits have been repeatedly observed of three year old asexually propagated progeny of my new variety growing in Dearing, Ga., and are determined to be the unique characteristics of the new *Thuja occidentalis* plant variety 'RutThu#1':

1. Compact.
2. Dark green.

'RutThu#1' can be compared to 'Holmstrup'. 'RutThu#1' is shorter and more compact (31" high×24" wide) than 'Holmstrup' after seven years in the field at CANR.

BRIEF DESCRIPTION OF THE PHOTOGRAPHS

The accompanying colored photographic illustrations show the overall appearance and distinct characteristics of the new cultivar of *Thuja occidentalis*. The colors in the photographs are as close as possible with the photographic and printing technology utilized.

FIG. 1 is a photograph of a six-year old *Thuja* 'RutThu#1' planted in Dearing, Ga. The plant in this photograph is 28 inches tall by 26 inches wide.

DETAILED BOTANICAL DESCRIPTION

Throughout this specification, color names beginning with a small letter signify that the name of that color, as used in common speech, is aptly descriptive. Color names beginning with a capital letter designate values based upon The R.H.S. Colour Chart, 5$^{th}$ Edition published by The Royal Horticultural Society, London, England.

The following is a detailed description of the botanical description of the new variety 'RutThu#1'. Where dimensions, sizes, colors, and other characteristics are given, it is to be understood that such characteristics are approximations and averages set forth as accurately as practicable. It should be noted that the phenotype of my new cultivar may vary with variations in environmental, climatic, and cultural conditions, as it has not been tested under all possible environmental conditions. The descriptions reported herein are largely from ten year old specimen 'RutThu#1' plants grown in Dearing, Ga. The foliage colors listed are for winter growth.

Plant type: Coniferous, evergreen.

Habit: Compact, rounded.

Size (inches):

*Height*.—31" (about 79 cm).

*Width*.—24" (about 61 cm).

Stem:

*Color*.—Greyed-Purple 183A. Scales: Greyed-Orange 165B.

*Length*.—8-20 cm.

*Diameter*.—Mature Trunk — 1 cm. Young Trunk — 5 mm. Lateral Branches — 2 mm.

*Pubescence*.—No pubescence, semi-glossy, smooth with some scales on younger stems. Scales shed with maturity.

*Shape*.—Round.

*Odor* (*of bruised stem*).—Moderately strong, pleasant evergreen (tansy) scent.

*Internode length*.—0.5-1 cm.

*Arrangement*.—Alternate.

*Branching*.—Main stem arises from base with numerous secondary branches, number of lateral branches average about 1 to 2 per cm of main stem.

*Branching aspect*.—Main stems upright. Lateral stems are at a typical angle of about 45 degrees from the main stem.

Leaf:

*Color* (*RHS*).—Winter tips — Greyed-Orange 165B, becomes Greyed-Orange 177A. Upper — Yellow-Green 146A. Lower — Yellow-Green 146B.

*Mature size* (*l*×*w*).—6-10 mm×1-2 mm.

*Apex*.—Acute.

*Base*.—Cuneate.

*Margin*.—Entire.

*Shape*.—Linear with scale-like structure.

*Lobes*.—None.

*Pubescence*.—None.

*Arrangement on stem*.—Alternate.

*Venation*.—None visible.

*Texture*.—Upper — glabrous, smooth, glossy. Lower — smooth, semi-glossy.

*Quantity*.—About 2 to 4 leaves per cm in lateral branches.

*Odor when crushed*.—Moderate intensity, pleasant evergreen (tansy) scent.

Flowers: No flowers have been observed.

Cone development: Neither male nor female cones have been observed.

Root description: Fibrous. Growth rate moderate.

Propagation: By hardwood cuttings.

Diseases and pests: No susceptibility or resistance to diseases or pests known to affect *Thuja* plants has been observed to date).

Cold hardiness: 'RutThu#1' has been observed to perform well in USDA Cold Hardiness Zone 8. The plant has not been tested in all hardiness zones. No damage was observed one winter when the temperatures dropped to 6° F.

What is claimed is:

1. A new and distinct cultivar of the *Thuja occidentalis* plant named 'RutThu#1' substantially as illustrated and described herein.

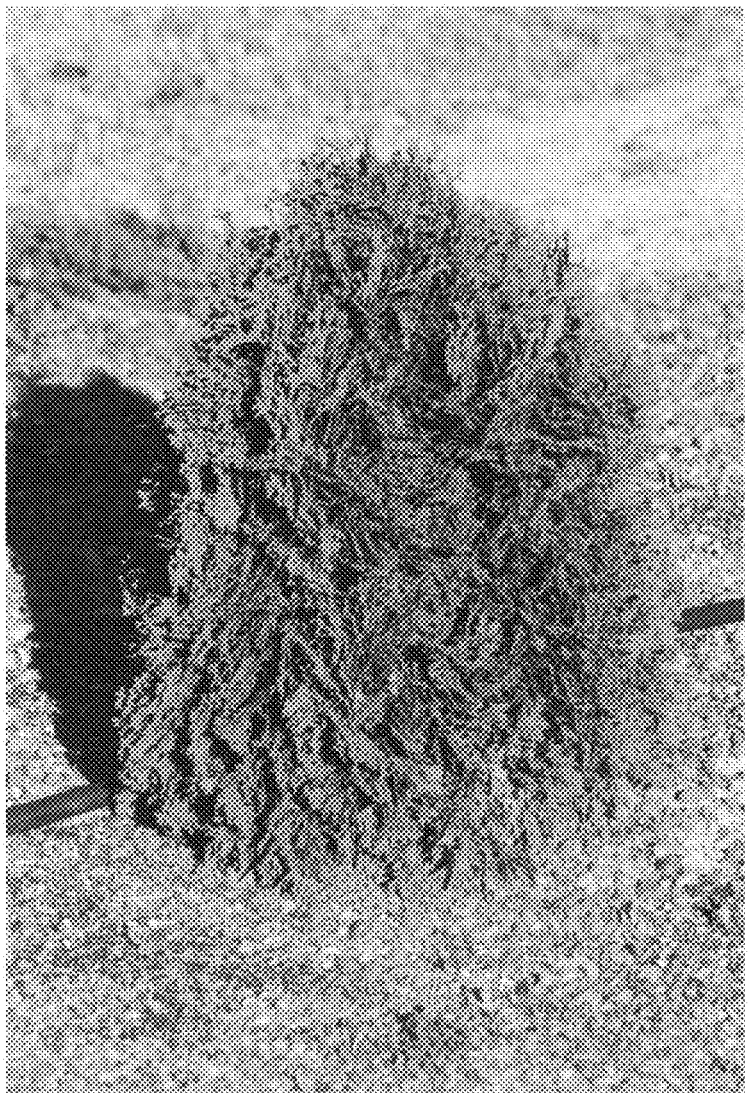

* * * * *